(12) United States Patent
Holman et al.

(10) Patent No.: US 12,189,846 B1
(45) Date of Patent: Jan. 7, 2025

(54) WEARABLE DEVICE WITH NON-OPTICAL SENSING NODES

(71) Applicants: David Holman, Etobicoke (CA); Roeland Petrus Hubertus Vertegaal, Perth Road Village (CA)

(72) Inventors: David Holman, Etobicoke (CA); Roeland Petrus Hubertus Vertegaal, Perth Road Village (CA)

(73) Assignee: HUAWEI TECHNOLOGIES CO., LTD., Shenzhen (CN)

( * ) Notice: Subject to any disclaimer, the term of this patent is extended or adjusted under 35 U.S.C. 154(b) by 0 days.

(21) Appl. No.: 18/346,832

(22) Filed: Jul. 4, 2023

(51) Int. Cl.
| G06F 3/01 | (2006.01) |
| A61B 5/00 | (2006.01) |
| A61B 5/026 | (2006.01) |
| A61B 8/06 | (2006.01) |
| A61B 8/08 | (2006.01) |

(52) U.S. Cl.
CPC .............. G06F 3/013 (2013.01); *A61B 5/026* (2013.01); *A61B 5/489* (2013.01); *A61B 8/06* (2013.01); *A61B 8/0891* (2013.01)

(58) Field of Classification Search
CPC ......... G06F 3/013; A61B 5/026; A61B 5/489; A61B 8/06; A61B 8/0891
USPC ....................................................... 345/156
See application file for complete search history.

(56) References Cited

U.S. PATENT DOCUMENTS

| 11,083,390 | B2 | 8/2021 | Holman | |
| 2002/0173725 | A1* | 11/2002 | Rock | A61N 1/39044 |
| | | | | 600/509 |
| 2010/0081941 | A1* | 4/2010 | Naghavi | A61B 5/02007 |
| | | | | 600/481 |
| 2020/0037994 | A1* | 2/2020 | Song | G01F 1/712 |
| 2020/0085306 | A1* | 3/2020 | To | A61B 5/681 |
| 2020/0253491 | A1* | 8/2020 | Nurmikko | A61B 5/0261 |
| 2020/0315571 | A1* | 10/2020 | Sonnenschein | A61B 8/4411 |
| 2021/0015446 | A1* | 1/2021 | Ritchie | A61B 5/021 |
| 2021/0153755 | A1* | 5/2021 | Srinivasan | G01L 1/24 |
| 2021/0353165 | A1* | 11/2021 | Galeev | A61B 5/7264 |
| 2022/0117503 | A1* | 4/2022 | Wang | A61B 5/14521 |
| 2023/0355204 | A1* | 11/2023 | Xu | A61B 8/565 |
| 2023/0408806 | A1* | 12/2023 | Talbert | A61B 1/045 |
| 2024/0099597 | A1* | 3/2024 | Srinivasan | A61B 5/02255 |

OTHER PUBLICATIONS

Constant, N et al."Pulse-Glasses: An unobtrusive, wearable HR monitor with Internet-of-Things functionality. Constant et al." IEEE Jun. 2015.

\* cited by examiner

*Primary Examiner* — Tom V Sheng

(57) ABSTRACT

A wearable device comprising a first array of non-optical sensing nodes is disclosed. The first array comprises a plurality of nodes. The plurality of nodes are operable to sense vasodilation of an artery in proximity to the first array. Systems and methods for determining a difference between a first position and a first reference position of the first array relative to a first artery are disclosed. First signal information may be received from the wearable device. The first signal information may represent first signal variation data sensed by each node of the first array. A first position of the first array relative to a first artery may be determined based on a first signal variation pattern in the first signal information. A difference between the first position and a first reference position of the first array relative to the first artery may then be determined.

22 Claims, 13 Drawing Sheets

```
┌─────────────────────────────────────────────────┐
│ Receive second reference signal information     │      1200
│ representing respective second reference signal │
│ variation data sensed by each node of a second  │
│ array of non-optical sensing nodes              │
│                    1210                         │
└─────────────────────────────────────────────────┘
                       │
                       ▼
┌─────────────────────────────────────────────────┐
│ Determine a second reference position of the    │
│ second array relative to a second artery        │
│                    1220                         │
└─────────────────────────────────────────────────┘
                       │
                       ▼
┌─────────────────────────────────────────────────┐
│ Receive second signal information representing  │
│ respective second signal variation data sensed  │
│ by each node of the second array of non-optical │
│ sensing nodes                                   │
│                    1230                         │
└─────────────────────────────────────────────────┘
                       │
                       ▼
┌─────────────────────────────────────────────────┐
│ Determine a second position of the second array │
│ relative to the second artery                   │
│                    1240                         │
└─────────────────────────────────────────────────┘
                       │
                       ▼
┌─────────────────────────────────────────────────┐
│ Determine a difference between the second       │
│ position and the second reference position      │
│                    1250                         │
└─────────────────────────────────────────────────┘
```

FIGURE 12

WEARABLE DEVICE WITH NON-OPTICAL SENSING NODES

RELATED APPLICATION DATA

This is the first patent application related to this matter.

FIELD

The present disclosure generally relates to wearable computing systems, and in particular, to wearable devices having non-optical sensing arrays.

BACKGROUND

When a wearable device is worn by a user, the position of the wearable device on the user may change over time, affecting the performance of the wearable device.

For example, when a wearable device, such as a pair of smartglasses is worn, the position of the wearable device relative to the user's face may change over time. This positional variance may negatively impact imaging algorithms, eye-tracking algorithms, and/or other solutions that rely on calibrating and/or assuming a fixed position of the glasses on the face.

In many cases, the user may be unaware that the position of the wearable device has shifted, leading to a suboptimal user experience with the wearable device.

Improvements to the field are desired.

SUMMARY

According to some aspects of the present disclosure, the position of a wearable device relative to the body part upon which the device is worn may be measured. The measurement may be performed by identifying and tracking features of one or more blood vessels within the body part. The one or more blood vessels may be used as anatomical landmarks.

In some examples, the wearable device may include an array of non-optical sensing nodes operable to sense vasodilation of an artery in proximity to the array. Localized skin surface perturbations caused by arterial pressure waveforms may be used to identify the position of the wearable device relative to the artery. Depending on the proximity of a node to the artery, individual nodes may sense a higher signal variation (overtop the artery) or a lower signal variation (nearby the artery).

In this way, an array of nodes with varied signal magnitudes may be used to track, over time, the position of the wearable device relative to the body part upon which the device is worn. In some examples, pulse rate, heart rate variability (HRV) and other biometric features related to cardiovascular fitness, human activity recognition, health, and wellness, may be determined through sensing of vasodilation via the array.

In embodiments where capacitive sensing nodes are used as non-optical sensing nodes, direct contact with the skin surface of the body part is not required to measure vasodilation. Such embodiments may be advantageous, as they may provide for continuous identification and tracking of the position of the artery under real-life conditions, where direct contact with a skin surface may not occur or may not be maintained.

In some existing technologies, photoplethysmography (PPG) sensors are sometimes used to facilitate the continuous and real-time monitoring of physiological conditions. However, use of PPG sensors to determine proximity to an artery is fraught with challenges. For example, PPG sensors are typically large and cannot be arranged to achieve the fine-grained spatial density required to localize arterial features, such as features of the angular artery. As well, PPG sensors use subdermal light scattering that reflects blood volume activity at a broad tissue level. This optical approach makes it difficult to localize specific anatomical landmarks, like the boundaries of an artery, and is also unsuitable for use close to the eyes.

In some examples, the wearable device comprises a device supported by the user's nose, such as a pair of smartglasses, an augmented reality (AR)/virtual reality (VR)/mixed reality (MR) headset, etc. In such examples, one or more of arrays of non-optical sensing nodes may be included at or near the nose bridge of the wearable device to localize vasodilation of the angular arteries near the nasalis muscle.

In some implementations where an array of non-optical sensing nodes is provided on each side of the nose bridge of the wearable device, dual measurements of cardiac activity (e.g., HRV) may be provided. The differences between these measurements may be used to infer subtle information about the position of the wearable device. For example, if the non-optical sensing nodes are pressure-sensing nodes, then higher signal amplitudes sensed by the array at the left side of the nose bridge may indicate a closer proximity of the wearable device to the left nose bridge (and hence greater pressure sensed), and may indicate that the wearable device is pressing inwards and rightwards with respect to the face. In another example, if the non-optical sensing nodes are capacitive-sensing nodes (e.g., parallel plate capacitive-sensing nodes), then lower signal amplitudes sensed by the array at the left side of the nose bridge may indicate closer proximity of the wearable device to the left nose bridge (since skin is conductive and draws away capacitance from the parallel plates, lower sensed capacitance indicates closer proximity to skin), and may similarly indicate that the wearable device is shifted inwards and rightwards with respect to the face.

Examples of the present disclosure may provide for tracking when and how the wearable device moves about a user's face during wear.

Examples of the present disclosure may provide for detecting whether the wearable device is worn correctly or incorrectly (e.g., too far down nose bridge and/or not secured on the face).

Examples of the present disclosure may provide for detecting whether the wearable device is pushing too much to the left or right on the user's nose.

Examples of the present disclosure may provide a dual measurement of heart rate variability (HRV) via the angular arteries to detect stress, emotional arousal, mental health, and to estimate cognitive load.

Examples of the present disclosure may provide a dual measurement of pulse wave velocity (PWV) via the angular arteries to detect arterial stiffness (an indicator of health and fitness). In some examples, PWV measurements may be paired with other wearable devices (e.g. smartwatch).

Examples of the present disclosure may provide for detecting and classifying changes in human movement and activity (e.g., signal variations may occur during moments of increased activity such as rapid head movement, sneezing, etc.).

In accordance with an example aspect of the present disclosure, there is provided a wearable device comprising a first array of non-optical sensing nodes, the first array comprising a plurality of nodes, wherein the plurality of nodes are operable to sense vasodilation of an artery in proximity to the first array.

In some implementations, the non-optical sensing nodes comprise at least one of capacitive sensing nodes or vibration sensing nodes.

In some implementations, the first array is positioned at a first side of a nose bridge of the wearable device.

In some implementations, the wearable device further comprises a second array of non-optical sensing nodes. The second array may comprise another plurality of nodes, and the second array may be positioned at a second side of the nose bridge of the wearable device.

In some implementations, the wearable device is a pair of smartglasses, and the first array is positioned at a first side of a nose bridge of the smartglasses.

In some implementations, the wearable device is an extended reality (XR) headset, and the first array is positioned at a first side of a nose bridge of the XR headset.

In some implementations, the wearable device further comprises a wireless communication interface configured to transmit signal information representing data sensed by the first array to a computing system.

In some implementations, the plurality of nodes in the first array are arranged in at least two columns and at least two rows.

In another example aspect, the present disclosure describes a computer-implemented method. The method comprises receiving, from a wearable device, first signal information representing respective first signal variation data sensed by each node of a first array of non-optical sensing nodes of the wearable device. The method further comprises determining a first position of the first array relative to a first artery based on a first signal variation pattern in the first signal information; and determining a difference between the first position and a first reference position of the first array relative to the first artery.

In an example of the preceding example aspect of the method, the difference between the first position and the first reference position is determined to be a compensable displacement, and the method further comprises applying the compensable displacement to a tracked eye position.

In an example of any of the preceding example aspects of the method, prior to applying the compensable displacement to the tracked eye position, the method further comprises receiving eye gaze signal information; and determining the tracked eye position based on the received eye gaze signal information.

In an example of any of the preceding example aspects of the method, the difference between the first position and the first reference position is determined to be outside of a tolerance range, and the method further comprises outputting a notification to adjust the wearable device.

In an example of any of the preceding example aspects of the method, the method further comprises, prior to receiving the first signal information from the wearable device: receiving, from the wearable device, first reference signal information representing respective first reference signal variation data sensed by each node of the first array of non-optical sensing nodes of the wearable device; and determining a first reference position of the first array relative to a first artery based on a first reference signal variation pattern in the first reference signal information.

In an example of any of the preceding example aspects of the method, the method further comprises, prior to determining the first reference position: determining that the first reference signal information indicates a first low frequency signal similar to human heart activity. The first reference position may be determined in response to determining that the first reference signal information indicates the first low frequency signal similar to human heart activity.

In an example of any of the preceding example aspects of the method, the method further comprises: receiving, from a wearable device, second signal information representing respective second signal variation data sensed by each node of a second array of non-optical sensing nodes of the wearable device; determining a second position of the second array relative to a second artery based on a second signal variation pattern in the second signal information; and determining a difference between the second position and a second reference position of the second array relative to the second artery.

In an example of any of the preceding example aspects of the method, the method further comprises, prior to determining the second signal information from the second array of non-optical sensing nodes: receiving, from the wearable device, second reference signal information representing respective second reference signal variation data sensed by the second array of non-optical sensing nodes of the wearable device; and determining the second reference position of the second array relative to the second artery based on a second reference signal variation pattern in the second reference signal information.

In an example of any of the preceding example aspects of the method, prior to determining a the second reference position, the method further comprises: determining that the first reference signal information indicates a first low frequency signal similar to human heart activity; determining that the second reference signal information indicates a second low frequency signal similar to human heart activity; and determining that the first low frequency signal and the second low frequency signal have similar magnitudes.

In an example of any of the preceding example aspects of the method, the first position of the first array relative to the first artery is determined by generating a first matrix of measurements based on the first signal information. The first reference position of the first array relative to the first artery is determined by generating a first reference matrix of measurements based on the first reference signal information; and wherein the difference between the first position and the first reference position is determined based on a comparison between the first matrix and the first reference matrix.

In an example of any of the preceding example aspects of the method, the first position is determined by: identifying a first set of one or more nodes of the first array, wherein the respective first signal variation data sensed by each node of the first set indicates higher signal variation than the respective first signal variation data sensed by each of the one or more nodes not of the first set. The first reference position may be determined by: identifying a first reference set of one or more nodes of the first array, wherein the respective first reference signal variation data sensed by the one or more nodes of the first reference set indicates higher signal variation than the respective first reference signal variation data sensed one or more nodes not of the first reference set.

In an example of any of the preceding example aspects of the method, the difference between the first position and the first reference position is determined based on a comparison between a location of the first set of one or more nodes in the first array and a location of the first reference set of one or more nodes in the first array.

In an example of any of the preceding example aspects of the method, the first position is further determined by identifying a first node of the first set, the first node having two or more neighbour nodes belonging to the first set. The first reference position may be determined by identifying a first reference node of the first reference set, the first reference node having two or more neighbour nodes belonging to the first reference set. The difference between the first position and the first reference position may be determined based on a comparison between a location of the first node of the first set and a location of the first reference node of the first reference set.

In accordance with yet another example aspect of the present disclosure, there is provided a computing system comprising a processor, and a memory coupled to the processor. The memory may store instructions which, when executed by the processor, cause the computing system to: receive, from a wearable device, first signal information representing respective first signal variation data sensed by each node of a first array of non-optical sensing nodes of the wearable device; determine a first position of the first array relative to a first artery based on a first signal variation pattern in the first signal information; and determine a difference between the first position and a first reference position of the first array relative to the first artery.

In another example aspect, the present disclosure describes a non-transitory computer readable medium having machine-readable instructions which, when executed by an apparatus, cause the apparatus to perform any preceding examples of the preceding example aspects of the methods.

In another example aspect, the present disclosure describes an apparatus comprising a processing unit and a memory including instructions that, when executed by the processing unit, cause the apparatus to perform any preceding examples of the preceding example aspects of the methods.

In another example aspect, the present disclosure describes an apparatus comprising a receiving module configured to carry out the receiving steps of any preceding example aspects of the methods.

In another example aspect, the present disclosure describes a processing module configured to control an apparatus to cause the apparatus to carry out any preceding example aspects of the methods.

In another example aspect, the present disclosure describes a system chip comprising a processing unit configured to execute instructions to cause an apparatus to carry out any preceding example aspects of the methods.

In another example aspect, the present disclosure describes a computer program characterized in that, when the computer program is run on a computer, the computer is caused to execute any preceding example aspects of the methods.

BRIEF DESCRIPTION OF THE DRAWINGS

Reference will now be made, by way of example, to the accompanying drawings which show example embodiments of the present disclosure, and in which:

FIG. 12 is a flowchart of an example method of determining a difference between a second position and a second reference position, in accordance with examples of the present disclosure.

Similar reference numerals may have been used in different figures to denote similar components.

DESCRIPTION OF EXAMPLE EMBODIMENTS

In the present disclosure, the term "XR" refers to "extended reality", which includes virtual reality (VR), augmented reality (AR), and mixed reality (MR) for the purposes of this disclosure. As used herein, XR refers to the presentation of virtual visual elements to a user through an XR display.

In the present disclosure, statements that a second element is "based on" a first element mean that characteristics of the second element are affected or determined at least in part by characteristics of the first element. The first element may be considered an input to an operation or calculation, or a series of operations or computations, which produces the second element as an output that is not independent from the first element.

Figure 1:
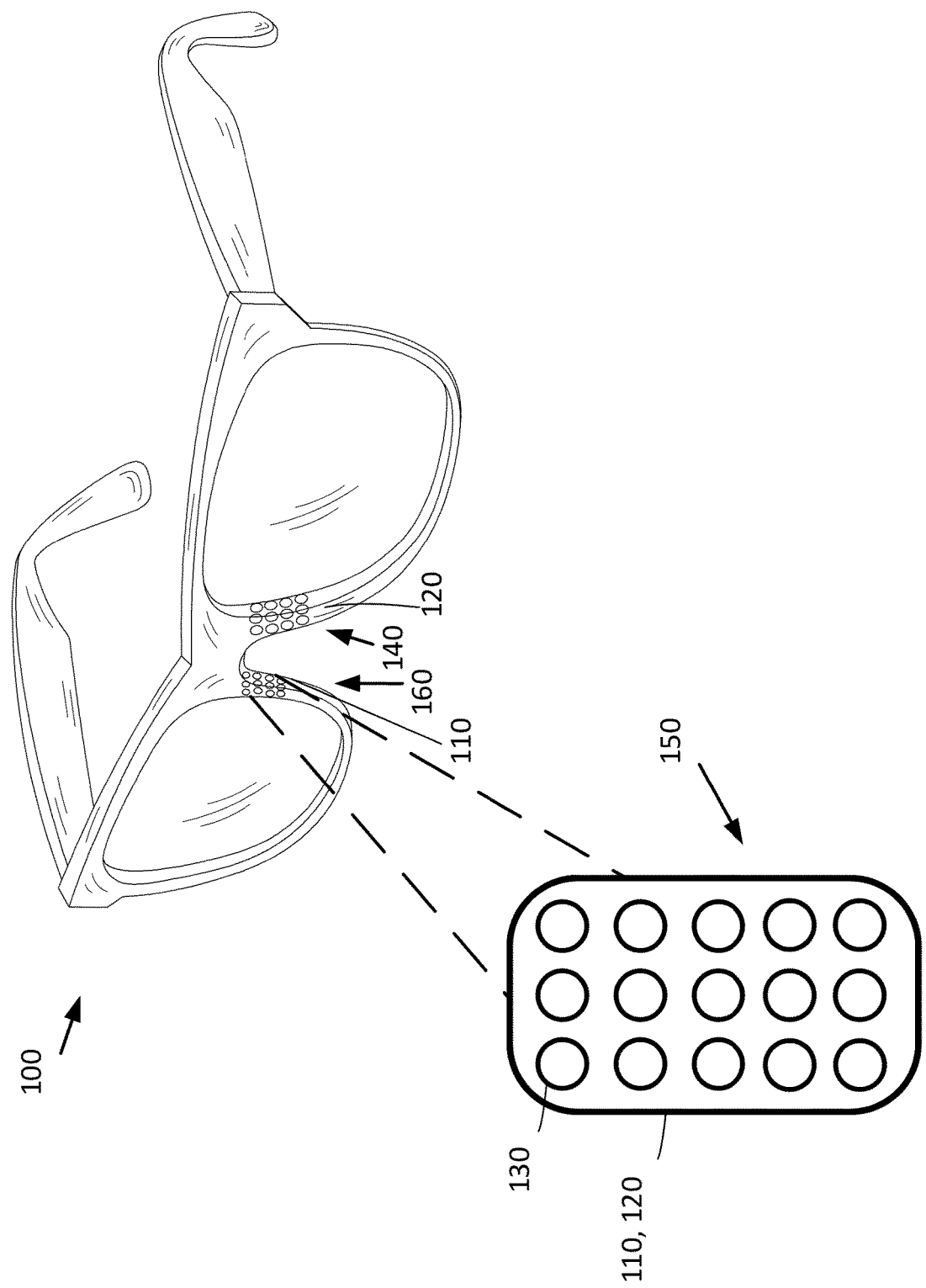
FIG. 1 is a schematic diagram illustrating an example wearable device, including a close-up view of a first array of the wearable device, in accordance with examples of the present disclosure.

Reference is first made to FIG. 1, which is a schematic diagram illustrating an example wearable device 100, including a close-up view 150 of a first array 110 of the wearable device 100, in accordance with examples of the present disclosure. While the wearable device 100 illustrated in FIG. 1 is a pair of smartglasses, the embodiments described herein are not so limited. For example, the wearable device may be a VR/AR/MR/XR headset, a smart watch or a smartring, among other possibilities.

As illustrated, the example wearable device 100 includes a first array 110 and a second array 120 of non-optical sensing nodes. As shown, the first array 110 is positioned at a first nose pad region 160 at a first side of a nose bridge of the wearable device 100, and the second array 120 is positioned at a second nose pad region 140 at a second side of the nose bridge of the wearable device 100.

In some embodiments, the wearable device 100 may include only the first array 110. In some embodiments, the wearable device 100 may include two or more arrays.

As shown in the close-up view 150 of the representation of both the first and second arrays 110, 120, the first and second arrays 110, 120 each contain a plurality of non-optical sensing nodes 130. The non-optical nodes 130 may be, for example, self-capacitive sensing nodes, mutual capacitive sensing nodes and/or vibration sensing nodes (such as micro-electromechanical systems (MEMS) sensors, piezoelectric sensors and/or electromagnetic sensors) operable to sense vasodilation of an artery in proximity to the first array. In some examples, each node 130 may be a parallel plate capacitor, however it should be understood that other types of capacitive-sensing nodes may be used. In some embodiments, such as when the nodes 130 are capacitive sensing nodes, direct contact with a skin surface is not required to measure vasodilation. In the case of capacitive sensing nodes, capacitive change caused by skin surface perturbations relating to vasodilation may be transmitted through air or other similar dielectric materials. In some embodiments, such as when the nodes 130 are vibration sensing nodes, direct contact with a skin surface may be required, as vibrations can be more efficiently transmitted through a dense material (e.g., plastic).

The first array 110 is shown as having a plurality of nodes 130 arranged in three columns and five rows (3×5). However, the present disclosure is not limited to this topography. In some embodiments, the plurality of nodes 130 in the first array may be arranged in at least two columns and at least two rows (2×2). In yet other embodiments, the plurality of nodes 130 of the first array 110 may be arranged in any suitable topography (e.g., a single column, a single row, diagonally, etc.).

While the example wearable device 100 is illustrated as a pair of smartglasses, the wearable device 100 may also be another wearable device 100 having a nose bridge, such as an AR/VR/MR/XR headset. The wearable device 100 may also be a wearable device 100 without a nose bridge, such as a smartwatch, or a smartring, for example.

The first and second arrays 110, 120 of non-optical sensing nodes 130 may be operable to measure vasodilation of an artery. For example, the first and second arrays 110, 120 of non-optical sensing nodes 130 may be self-capacitance nodes, mutual capacitance nodes, and/or vibrational nodes, for example. When placed on or near the skin, localized skin surface perturbations caused by arterial pressure waveforms traveling through the body may be detected and measured.

Figure 2B:
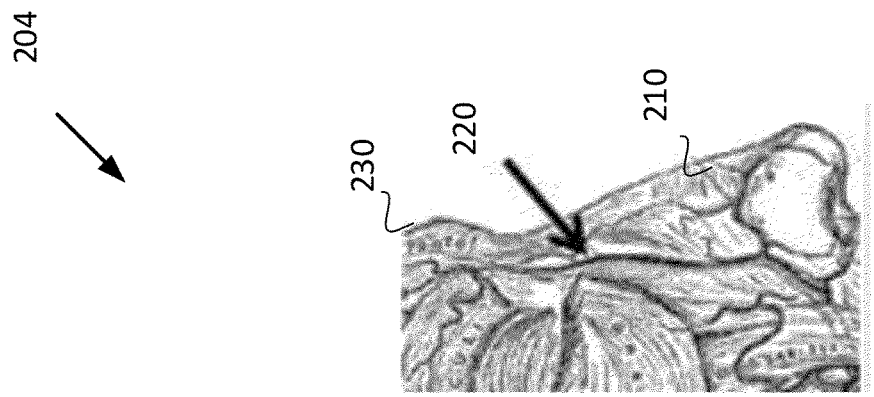
FIG. 2B is a sub-epidermal profile view of an upper portion of a human face, including the nose, and showing the interior blood vessels, in accordance with examples of the present disclosure.
Figure 2A:
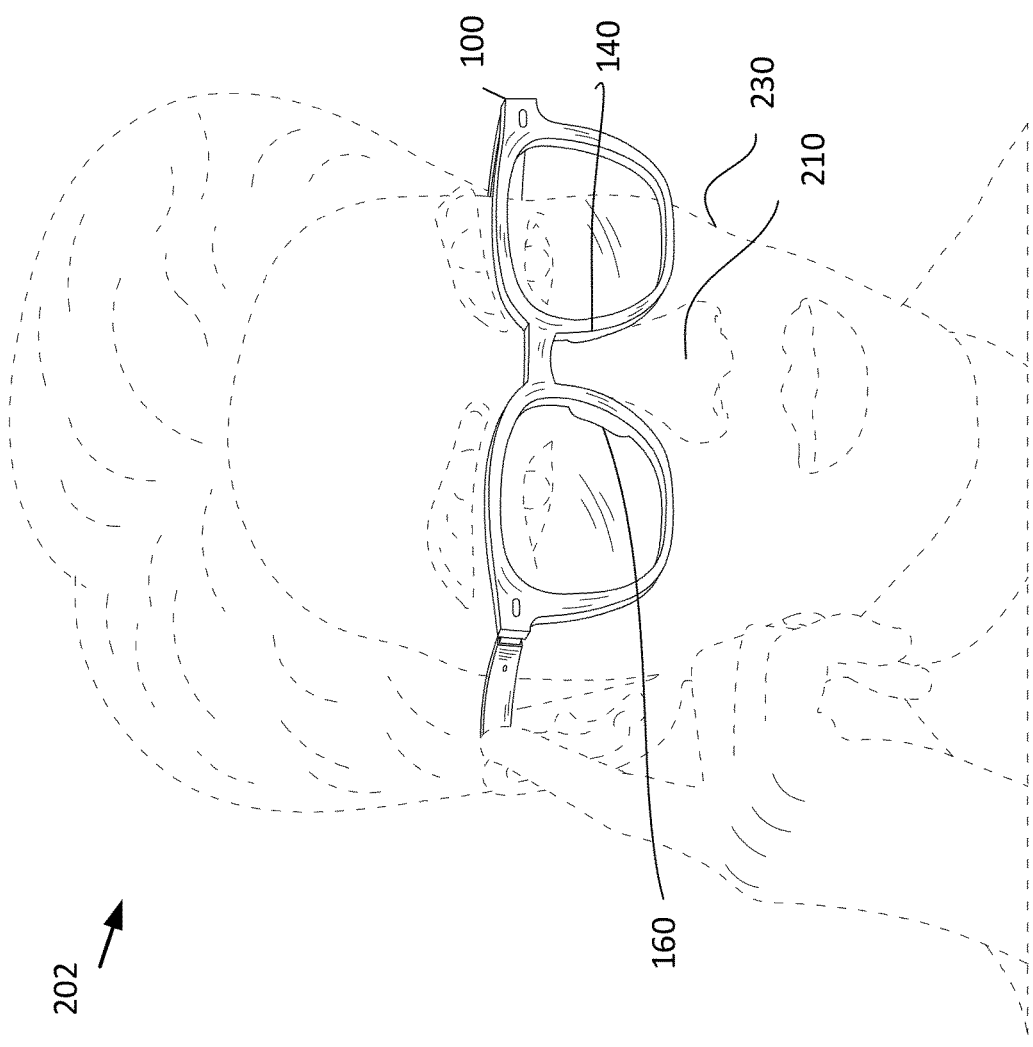
FIG. 2A shows a user wearing an example wearable device of a pair of smartglasses, in accordance with examples of the present disclosure.

FIG. 2A shows a user 202 wearing the wearable device 100, where the wearable device 100 is embodied as a pair of smartglasses, in accordance with examples of the present disclosure. The first and second nose pad regions 160, 140 are shown at the nose bridge of the wearable device 100, positioned on either side of the user's nose 210 when the wearable device 100 is worn by the user 202.

FIG. 2B is a sub-epidermal profile view 204 of an upper portion of a human face 230, including the nose 210, and showing the interior blood vessels, in accordance with examples of the present disclosure. A first angular artery 220 is shown extending laterally along the nose 210, near the convergence of the nose 210 with the face 230.

As can be seen with reference to FIG. 2A, the position of the first and second nose pad regions 160, 140 of the wearable device 100 align with the position of the first angular artery 220 (FIG. 2B) and the second angular artery (not shown) on either side of the user's nose 210, when the wearable device 100 is worn by the user 202. Due to this arrangement, the non-optical sensing nodes 130 (FIG. 1) of the wearable device 100, when worn by a user 202, may sense vasodilation of one or more angular arteries 220. Accordingly, localized skin surface perturbations caused by arterial pressure waveforms traveling through the body of the user 202 may be used to identify the positon of the wearable device 100 relative to one or more angular arteries 220.

In some examples, nodes 130 located directly over an angular artery 220 may sense a higher signal variation with respect to vasodilation of the angular artery 220. In some examples, nodes 130 located peripheral to an angular artery 220 may sense a lower signal variation with respect to vasodilation of the angular artery 220.

Figure 3:
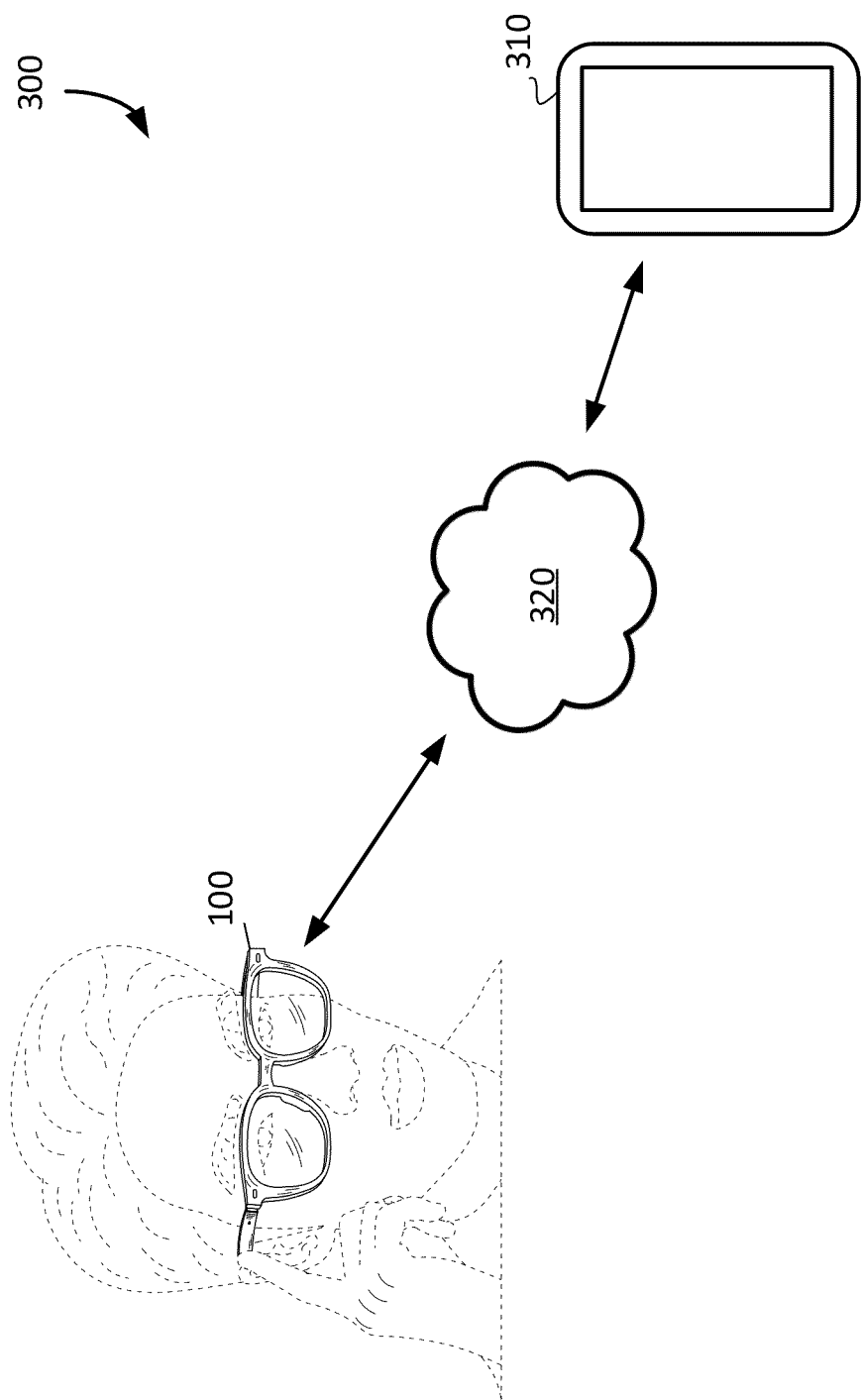
FIG. 3 is a schematic diagram illustrating a first operating environment of an example embodiment, in accordance with examples of the present disclosure.

FIG. 3 is a schematic diagram illustrating a first operating environment 300 of an example embodiment, in accordance with examples described herein. As shown in FIG. 3, the wearable device 100 may communicate with a user device 310, for example via a network 320. In other examples, the wearable device 100 may communicate with the user device 310 without requiring any network (e.g., over a direct communication link).

The network 320 may be a computer network, and may be a wired or wireless network, or some combination thereof. In some embodiments, the network 320 may be or may include a personal area network (PAN) and may use a connectivity protocol such as Wi-Fi, ZigBee, infrared and/or Bluetooth. In some embodiments, the network 320 may be or may include a public network, such as the Internet.

Both the user device 310 and the wearable device 100 may be computing systems. Alternatively, the user device 310 may be a computing system and the wearable device 100 may be an input device that may provide sensed data to the user device 310. While illustrated as a smartphone, the user device 310 may be another type of computing system such as a laptop, a tablet, a desktop computer, or the like. The user device 310 and the wearable device 100 may communicate (e.g., via the network 320) in order to identify and track features of one or more blood vessels within the body part upon which the wearable device 100 is worn. In some examples, the user device 310 and the wearable device 100 may communicate in order to determine whether the wearable device is worn correctly. In some implementations, the user device 310 and the wearable device 100 may communicate in order to track eye gaze of the user of the wearable device.

The wearable device 100 and the user device 310 may be in geographically disparate locations. Put differently, each of the wearable device 100 and the user device 310 may be remote from one another. Alternatively, in some embodiments, the wearable device 100 may include the user device 310 (e.g., the wearable device 100 may be a wearable computer, and functions of the user device 310 may be functions of the wearable device 100).

Figure 4:
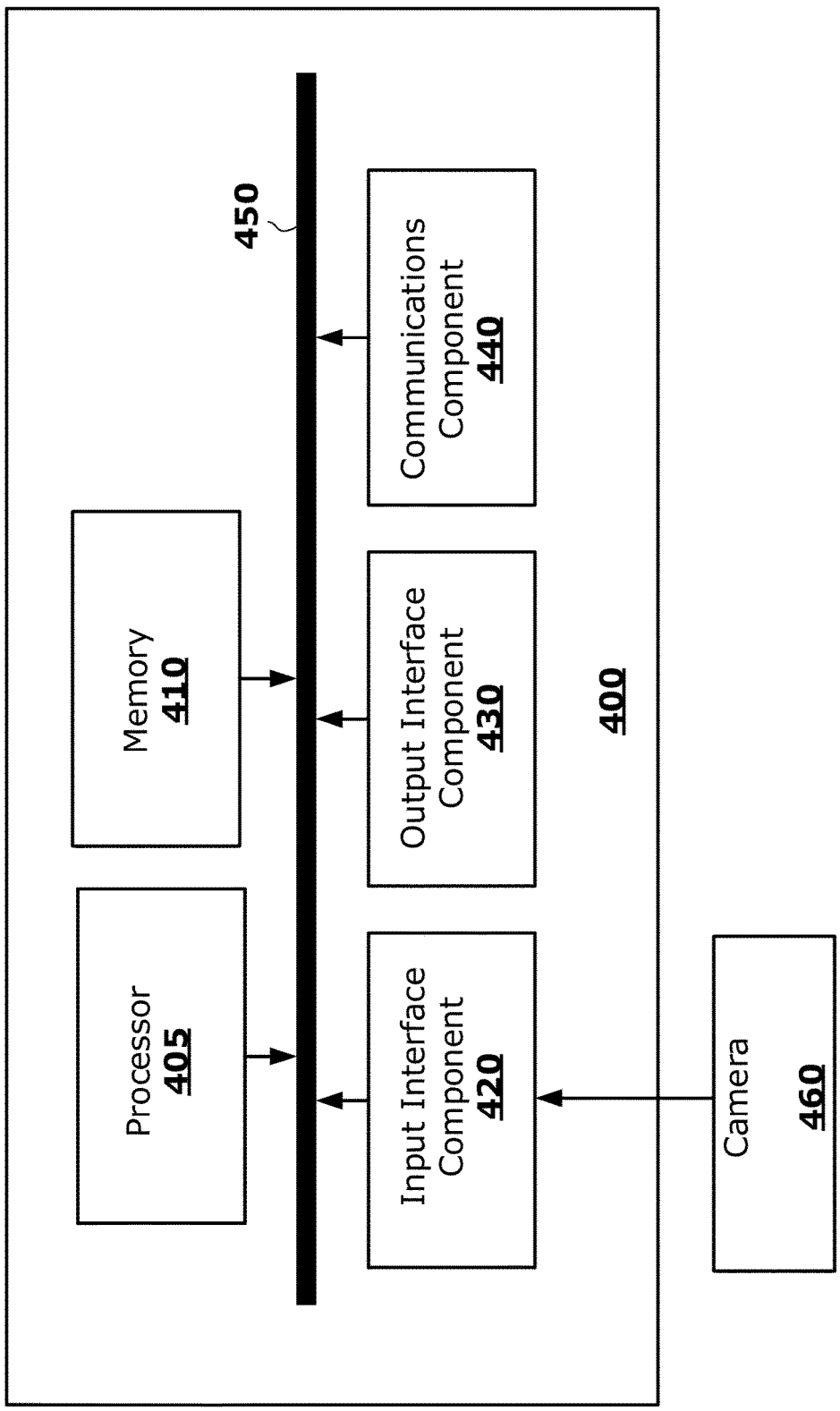
FIG. 4 is a high-level operation diagram of an example computing system.

FIG. 4 is a high-level operation diagram of an example computing system 400. In at least some embodiments, the example computing system 400 may be exemplary of one or more of the wearable device 100 (FIG. 3) and/or the user device 310 (FIG. 3), and is not intended to be limiting.

The example computing system 400 includes a variety of components. For example, as illustrated, the example computing system 400 may include a processor 405, a memory 410, an input interface component 420, an output interface component 430, and a communications component 440. As illustrated, the foregoing example components of the example computing system 400 are in communication over a bus 450.

The processor 405 is a hardware processor. The processor 405 may, for example, be one or more of a microprocessor, a digital signal processor, an application-specific integrated circuit (ASIC), a field-programmable gate array (FPGA), a dedicated logic circuitry, a dedicated artificial intelligence processor unit, a graphics processing unit (GPU), a tensor processing unit (TPU), a neural processing unit (NPU), a hardware accelerator, or combinations thereof.

The memory 410 allows data to be stored and retrieved. The memory 410 may include, for example, random access memory, read-only memory, and persistent storage. Persistent storage may be, for example, flash memory, a solid-state drive or the like. Read-only memory and persistent storage are a computer-readable medium. A computer-readable medium may be organized using a file system such as may be administered by an operating system governing overall operation of the example computing system 400.

The input interface component 420 allows the example computing system 400 to receive input signals. The input interface component 420 may serve to interconnect the example computing system 400 with one or more input devices. Input signals may be received from input devices by the input interface component 420. For example, where the example computing system 400 operates as the wearable device 100, the input interface component may receive input signals from one or more arrays (110, 120) of non-optical sensing nodes disposed on the wearable device 100 (FIG. 1). The input signals may correspond to localized skin surface perturbations caused by arterial pressure waveforms traveling through the body. In some embodiments, all or a portion of the input interface component 420 may be integrated with an input device.

As another example, the input interface component 420 may receive input signals from an eye tracking device, which be or may include at least one camera 460 capable of capturing images of at least one eye of a user of the wearable device 100. While shown as located outside of the example computing system 400, it will be understood that the camera 460 may be integrated with the input interface component 420.

In some embodiments, input devices may, for example, include one or more of a touchscreen, a touchpad, a button, a keyboard, a trackball, haptic gloves, a camera, or the like. The user device 310 (FIG. 3) may include a touch receiver which may be an input device, such as a touch pad, a touch screen, or a button.

The output interface component 430 allows the example computing system 400 to provide output signals. Some output signals may, for example allow provision of output to a user. The output interface component 430 may serve to interconnect the example computing system 400 with one or more output devices. Output signals may be sent to output devices by output interface component 430. For example, the user device 310 (FIG. 3) may include output devices such as, for example, a display screen such as a liquid crystal display (LCD), a touchscreen display, or the like. Additionally, or alternatively, output devices may include devices other than screens such as, for example, a speaker and/or a printer. In some embodiments, all or a portion of the output interface component 430 may be integrated with an output device.

The communications component 440 allows the example computing system 400 to communicate with other electronic devices and/or various communications networks. For example, the communications component 440 may allow the example computing system 400 to send or receive communications signals. The communications component may include a wireless communication interface. Communications signals may be sent or received according to one or more protocols or according to one or more standards. For example, the communications component 440 may allow the example computing system 400 to communicate via a cellular data network, such as for example, according to one or more standards such as, for example, Global System for Mobile Communications (GSM), Code Division Multiple Access (CDMA), Evolution Data Optimized (EVDO), Long-term Evolution (LTE) or the like. Additionally, or alternatively, the communications component 440 may allow the example computing system 400 to communicate using near-field communication (NFC), via Wi-Fi.™, using Bluetooth.™ or via some combination of one or more networks or protocols. In some embodiments, all or a portion of the communications component 440 may be integrated into a component of the example computing system 400. For example, the communications component may be integrated into a communications chipset.

Software comprising instructions is executed by the processor 405 from a computer-readable medium. For example, software may be loaded into random-access memory from persistent storage of memory 410 or other software source. Additionally, or alternatively, instructions may be executed by the processor 405 directly from read-only memory of memory 410.

Figure 5:
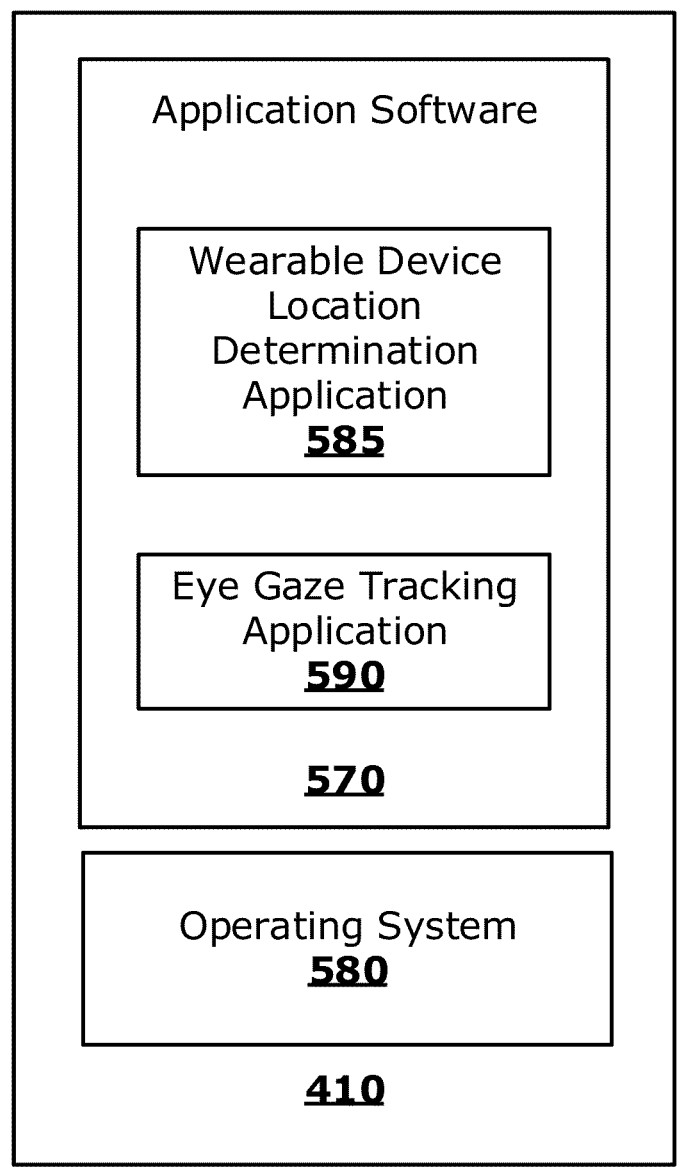
FIG. 5 depicts a simplified organization of software components stored in memory of the example computing system, in accordance with examples of the present disclosure.

FIG. 5 depicts a simplified organization of software components that may be stored in memory 410 of the example computing system 400. As illustrated, these software components include application software 570 and an operating system 580.

The application software 570 adapts the example computing system 400, in combination with the operating system 580, to operate as a system performing a particular function. In some embodiments, the application software 570 may comprise a wearable device location determination application 585 and/or an eye gaze signal tracking application 590.

The operating system 580 is software. The operating system 580 allows the application software 570 to access the processor 405, the memory 410, the input interface component 420, the output interface component 430, and the communications component 440. The operating system 580 may be, for example, Apple iOS™, Google™, Android™, Linux™, Microsoft™, Windows™, Harmony™, FreeRTOS™, or the like.

Figure 6:
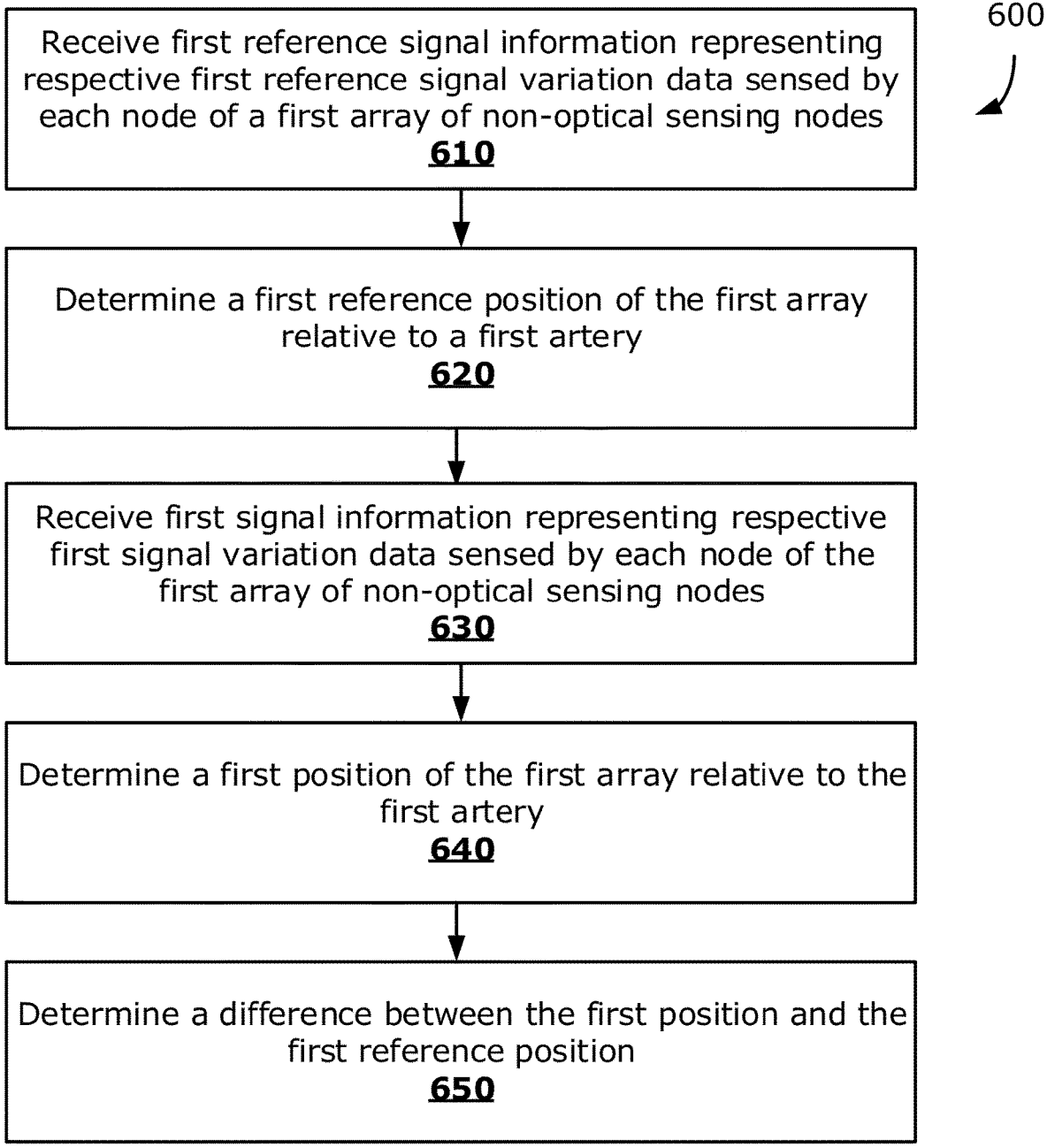
FIG. 6 is a flowchart of an example method of determining a difference between a first position and a first reference position, in accordance with examples of the present disclosure.

FIG. 6 is a flowchart of an example method 600 of determining a difference between a first position and a first reference position, in accordance with an embodiment of the present disclosure. The method 600 may be performed by one or more processors of a computing system. Specifically, the operations 610 and onward may be performed by one or more processors of a user device. The method 600 may be performed by the computing system 400 of FIG. 4, for example by the processor 405 executing instructions stored in the memory 410, such as instructions of the wearable device location determination application 585.

At the operation 610, the computing system receives first reference signal information representing respective first reference signal variation data sensed by each node of a first array of non-optical sensing nodes. The first reference signal information may be received from a wearable device (e.g., the wearable device 100 of FIG. 1), and the first array of nodes may form part of the wearable device (e.g., the first array 110 of non-optical sensing nodes 130).

At the operation 620, the computing system determines a first reference position of the first array relative to a first artery. The first reference position may be determined based on a first reference signal variation pattern in the first signal information.

The technique for determination of the first reference signal variation pattern may vary.

In some examples, the first reference signal variation pattern may be determined by generating a first reference matrix of measurement variations (e.g., as calculated over a defined period of time, such as 1 s) based on the first reference signal information, and the first reference signal variation pattern may be the positions of first reference matrix entries that have high variation.

In some examples, the first reference signal variation pattern may be defined as the locations of the nodes within the first array that sense higher signal variation.

As noted, nodes located directly over an angular artery may sense a higher signal variation (e.g., signal variation that exceeds a defined threshold) with respect to vasodilation of the angular artery, while nodes located peripheral to an angular artery may sense a lower signal variation (e.g., signal variation that does not exceed the defined threshold) with respect to vasodilation of the angular artery.

At the operation 630, the computing system receives first signal information representing respective first signal variation data sensed by each node of a first array of non-optical sensing nodes. The first signal information may be received from a wearable device (e.g., the wearable device 100 of FIG. 1), and the first array of nodes may form part of the wearable device (e.g., the first array 110 of non-optical sensing nodes 130).

At the operation 640, the computing system determines a first position of the first array relative to a first artery. The first position may be determined based on a first signal variation pattern in the first signal information.

As with the determination of the first reference signal variation pattern, the technique determination of the first signal variation pattern may vary. In general, the determination of the first signal variation pattern may be similar to the determination of the first reference signal variation pattern.

In some examples, the first signal variation pattern may be determined by generating a first matrix of measurement variations (e.g., as calculated over a defined period of time, such as 1 s) based on the first signal information, and the first signal variation pattern may be the positions of first matrix entries that have high variation.

In some examples, the first signal variation pattern may be defined as the locations of the nodes within the first array that sense higher signal variation.

At the operation 650, the computing system determines a difference between the first position and a first reference position of the first array relative to the first artery. In some examples, the difference may be categorized as a compensable displacement. In some examples, the difference may be determined to be outside of a tolerance range.

In some embodiments, prior to performing the method 600, the computing system may determine that the first reference signal information indicates a first low frequency signal similar to human heart activity. In some embodiments, the first reference position is determined in response to determining that the first reference signal information indicates the first low frequency signal similar to human heart activity.

It will be noted that the operations 630-650 may be performed independently of the operations 610-620. That is, a first reference position of the first array relative to the first artery may be determined and stored by the computing system, for example, in the memory 410 (FIG. 4). The operations 630-650 may be performed independently of the operations 610-620, for example the first reference position of the operation 650 may be retrieved from memory.

As noted, the technique for determination of the first reference signal variation pattern may vary. In some examples, the first signal variation pattern may be determined by generating a first reference matrix of measurements based on the first reference signal information, and the first reference signal variation pattern may be the positions of matrix entries that have high variation, as will now be discussed with reference to FIG. 7

Figure 7:
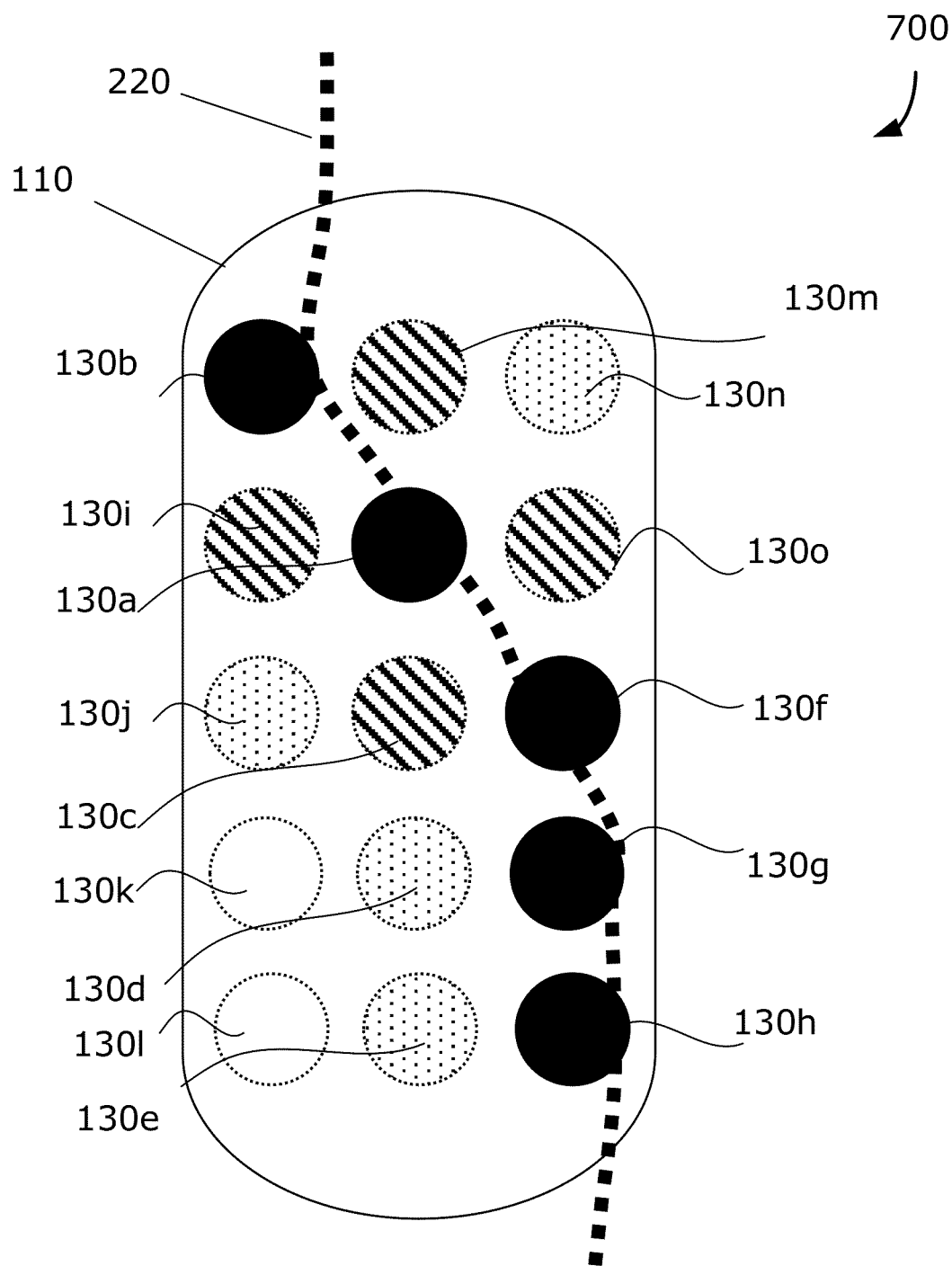
FIG. 7 is a first schematic close-up view of the first array adjacent the nose at the first angular artery, in accordance with examples of the present disclosure.

FIG. 7 is a first schematic close-up view 700 of the first array 110 adjacent the nose at the first angular artery 220 (represented by a dashed line), in accordance with examples of the present disclosure. The first array is illustrated as having three columns and five rows (3×5) of nodes 130a-130o (generically referred to as nodes 130).

The first array 110 is illustrated adjacent the nose 210 at the first angular artery 220, at a position corresponding to the location of the first nose pad region 160 (FIG. 1) of the wearable device 100 (FIG. 1) when worn in a reference position.

The path of the first angular artery 220 with respect to the nodes 130 of the first array 110 is shown in the first schematic profile view 700. The first angular artery 220 can be seen overlaid by the node 130b at the leftmost position of the first row of the first array 110, overlaid by the node 130a at the middle position of the second row of the first array 110, and overlaid by the nodes 130f, 130g, 130h at the rightmost positions of the third, fourth and fifth rows of the first array 110.

In the embodiment shown by FIG. 7, the vasodilation sensed by the nodes above the first angular artery 220 (namely, the leftmost node of the first row, the middle node of the second row, and the respective last nodes of the third, fourth and fifth rows) will be higher than the vasodilation sensed by the remaining nodes, due to the location of the first angular artery 220 with respect to each node. The nodes sensing the higher vasodilation may be identified as a first reference set of the first array 110, and may indicate the first reference position of the first array 110 relative to the first artery. The remaining nodes may be described as one or more nodes not of the first reference set of the first array 110.

The level of signal variation with respect to vasodilation of the angular artery 220 that is sensed by each node 130 has been represented by greyscale shading. For example, the vasodilation sensed by the nodes 130 overlaid by the first angular artery 220 (namely, the node 130b at the leftmost position of the first row of the first array 110, the node 130a at the middle position of the second row of the first array 110, and the nodes 130f, 130g, 130h at the rightmost positions of the third, fourth and fifth rows of the first array 110) are indicated in black.

The nodes 130 slightly peripheral to the first angular artery 220 (namely, the node 130m at the middle position of the first row of the first array 110, the nodes 130i, 130o at the leftmost and rightmost positions of the second row of the first array, and the node 130c at the middle position of the third row), are indicated in dark shading. The nodes 130 still more peripheral to the first angular artery 220 (namely, the node 130n at the rightmost position of the first row, the node 130j at the leftmost position of the third row, and the nodes 130k, 130l at the middle positions of the fourth and fifth rows) are indicated in light shading. The nodes 130 yet still more peripheral to the first angular artery 220 (namely, the nodes 130k, 130l at the leftmost positions of the fourth and fifth rows) are indicated in white. In this way, the relative level of vasodilation sensed by each node 130a-130o of the first array 110 is represented by a gradient of grey.

As noted, the first reference signal variation pattern may be the positions of matrix entries that have high variation, and may reflect the relative level of vasodilation as illustrated by the various levels of shading of the nodes 130 in FIG. 7.

For example, the levels of signal variation sensed by each of node 130 of the array 110 may be used to generate a first reference two-dimensional matrix of measurement variations reflecting vasodilation of the angular artery 220. In the example of FIG. 7, a 3×5 matrix of measurement variations may be generated. In some implementations, the information contained in the first reference matrix may be used to produce an image of the first angular artery 220 and related image sequences that may be processed using standard image techniques and/or deep learning.

For example, consider the array 110 shown in FIG. 7 in which the nodes 130 are arranged in regular rows and columns. The measurements from each node 130 may be represented as a respective intensity of signal from each node 130, which may be a numerical representation. The measurements over the array 110 may be min-max normalized and mapped to a range of 0-225 (e.g., a range corresponding to an 8-bit grayscale image). In this way, a grayscale image having 3×5 pixels may be produced from the measurements of the array 110 at a given moment in time. By obtaining such images over a period of time, the sequence of images may be compared with a reference image (obtained when the array 110 is at a reference position) to provide information about how the array 110 is moving relative to the reference position and thus how the wearable device 100 is moving as well.

In some examples, similarity between the node measurements in the first reference signal information and the current measurements in the first signal information may be used to determine how the position of the array 110 has changed. In this context, similarity (also referred to as a distance measure) may refer to the similarity between signal variation of a particular node in the first reference signal information and signal variation of a different node in the current first signal information. If the signal variation of a first node in the first reference signal information is now appearing instead in a different second node in the current first signal information, this may indicate that the second node is now at a position overtop the angular artery that was previously occupied by the first node. If the second node is located 3 mm closer to the tip of the wearer's nose compared to the first node, for example, this may indicate that the array 110 (and thus the wearable device 100) has moved 3 mm closer towards the wearer's face.

In another example, if the signal variations of all the nodes 130 in the current first signal information are similar to the signal variations of all the nodes 130 in the first reference signal information, but the nodes 130 in the current first signal information sense lower signal amplitudes, this may indicate that the array 110 (and the wearable device 100) has moved closer to the wearer's skin (e.g., because, if the nodes 130 are parallel plate capacitive-sensing nodes, sensed capacitance decreases as the distance between capacitive-sensing nodes 130 and the skin decreases).

The above examples illustrate a heuristic-based approach to map measurements from the array 110 (given reference measurements) to a function that determines the spatial positioning of the array 110, and thus the wearable device 100. Various existing image processing techniques or machine learning techniques may be used to implement this heuristic-based approach and compute the spatial positioning function.

In this way, the first signal variation pattern may be determined by generating a first reference matrix of measurement variations based on the first reference signal information, and the first reference signal variation pattern may be the positions of matrix entries that have high variation.

As further noted, in some examples, the first reference signal variation pattern may be defined as the locations of the nodes within the first array that sense higher signal variation, as will now be described with reference to FIG. 8.

Figure 8:
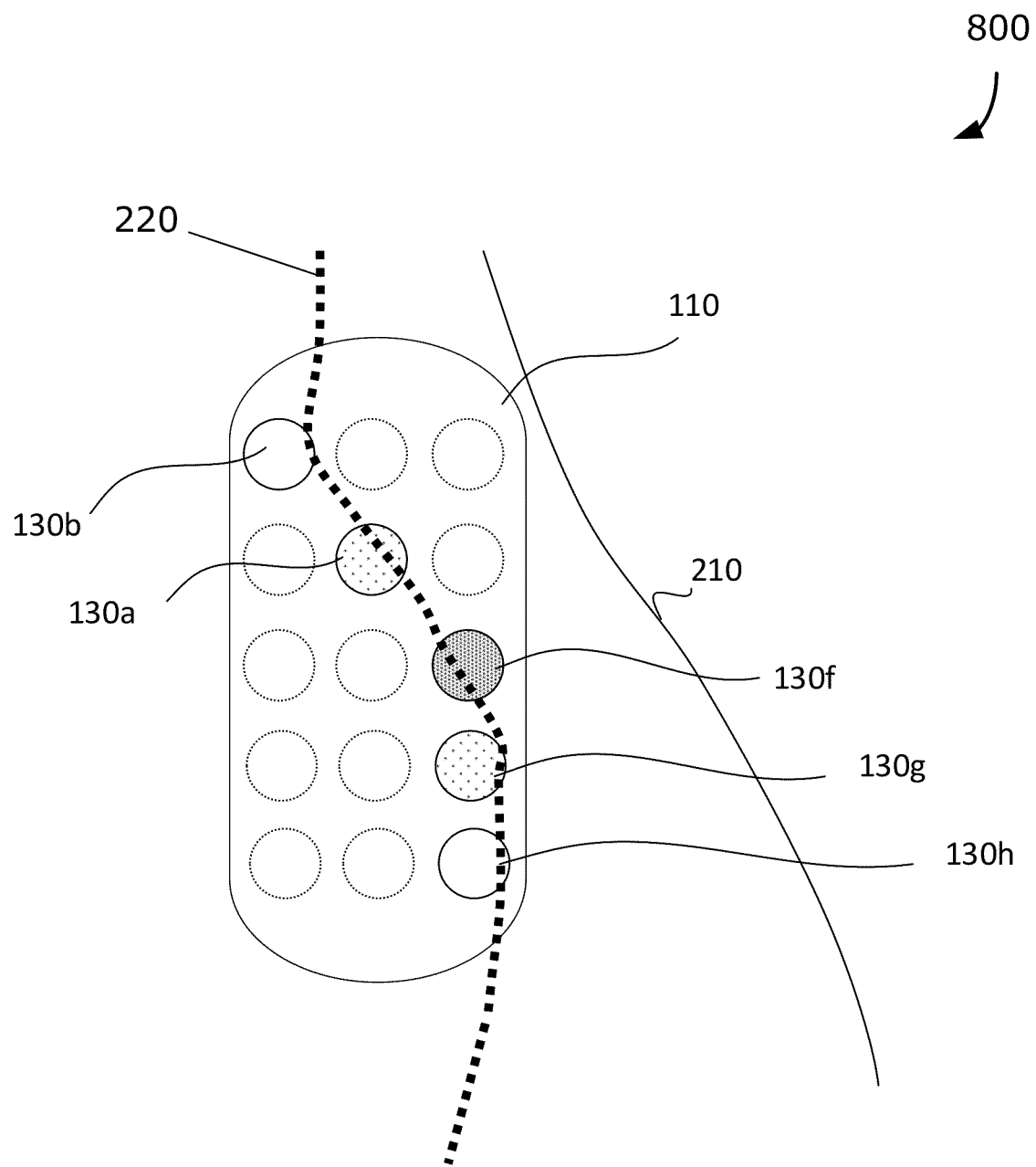
FIG. 8 is a second schematic close-up view of the first array adjacent the nose at the first angular artery, in accordance with examples of the present disclosure.

FIG. 8 is a second schematic close-up view 800 of the first array 110 adjacent the nose 210 at the first angular artery (represented by a dashed line), 220, in accordance with examples of the present disclosure. The first array is illustrated as having three columns and five rows (3×5) of nodes 130a-130o (generically referred to as nodes 130).

The first array 110 is illustrated adjacent the nose 210 at the first angular artery 220, at a position corresponding to the location of the first nose pad region 160 (FIG. 1) of the wearable device 100 (FIG. 1) when worn in a reference position.

The path of the first angular artery 220 with respect to the nodes 130 of the first array 110 is shown in the second schematic close-up view 800. The first angular artery 220 can be seen above the node 130b at the leftmost position of the first row of the first array 110, and above the node 130a at the middle position of the second row of the first array 110, and above the nodes 130fgh at the last positions of the third, fourth and fifth rows of the first array 110.

In the embodiment shown by FIG. 8, the nodes 130ab, 130fgh above the first angular artery may be described as belonging to the first reference set, as the vasodilation sensed by the nodes 130ab, 130fgh is higher than the vasodilation sensed by the remaining nodes of the first array 110. The remaining nodes may be described as one or more nodes not of the first reference set.

In some embodiments, the first reference node may be defined as a node having at least two neighbours belonging to the first reference set. In the example embodiment shown in FIG. 8, the node 130f at the last position of the third row is highlighted to identify the node 130f as the first reference node. The first reference node is highlighted to indicate that the first reference node has at least two neighbours belonging to the first reference set. In other words, the node 130f at the last position of the third row has been identified as having two or more neighbour nodes sensing a vasodilation higher than the vasodilation sensed by the nodes not of the first reference set. In the embodiment shown in FIG. 8, the node 130a at the middle position of the second row of the first array 110 and the node 130g at the last position of the fourth row of the first array 110 are highlighted to indicate that these nodes 130a, 130g represent two neighbours of the first reference node (the node 130f at the last position of the third row) belonging to the first set.

In this way, the first reference signal variation pattern may be defined as the relative level of vasodilation as illustrated by the highlighting of the nodes 130 in FIG. 8.

The first signal variation pattern may be determined using the same or similar approaches to determining the first reference signal variation pattern. As with the determination of the first reference signal variation pattern, the manner in which the first signal variation pattern may be determined may vary. In some examples, the first signal variation pattern may be determined by generating a first matrix of measurement variations based on the first signal information, as described in the context of the first reference signal variation pattern with reference to FIG. 7.

In some examples, the first signal variation pattern may be defined as the location of the nodes within the first array that sense higher signal variation, as described in the context of the first reference signal variation pattern with reference to FIG. 8.

A particular example of defining the first signal variation pattern as the location of the nodes within the first array that sense higher signal variation will now be discussed with reference to FIG. 9.

Figure 9:
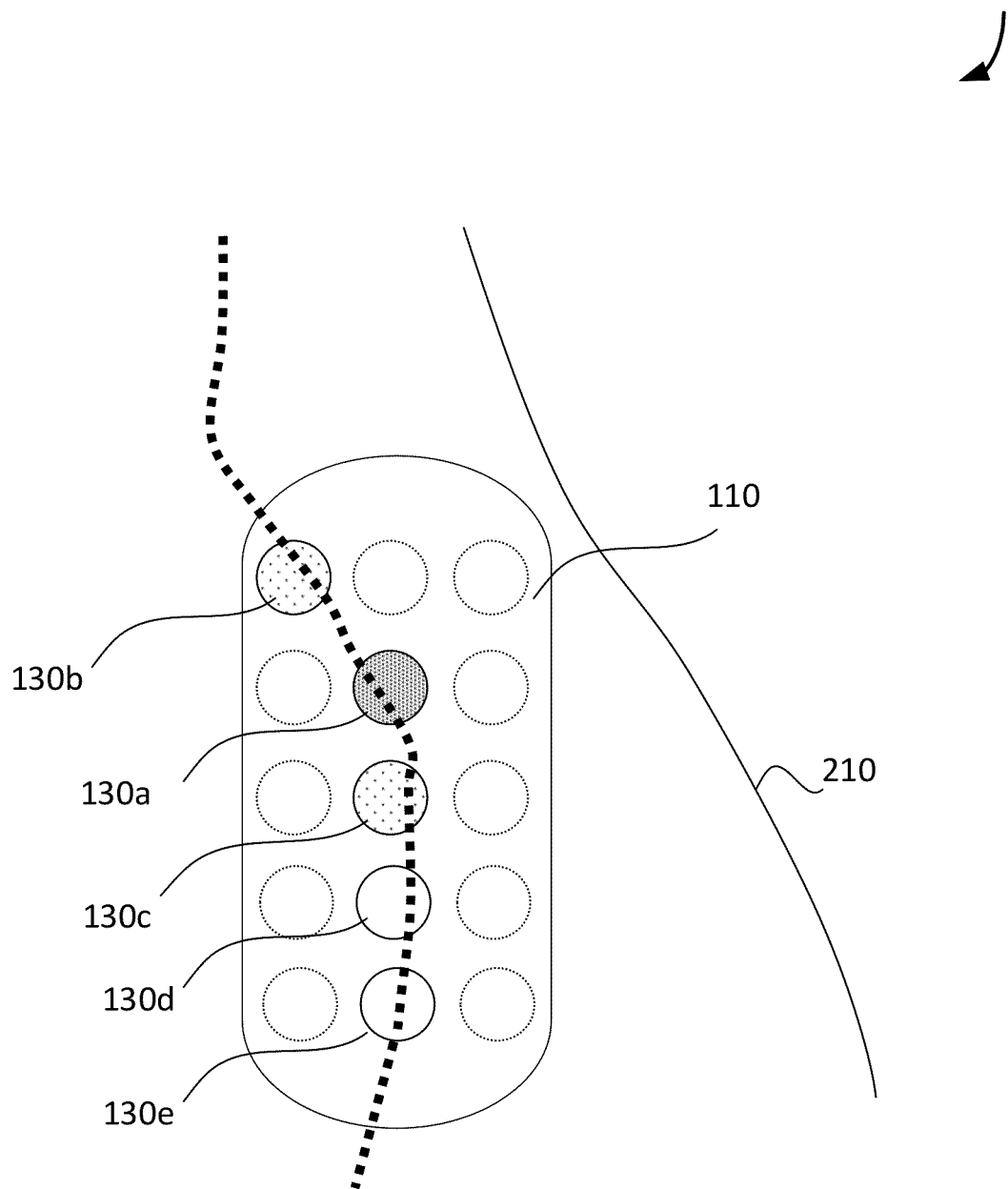
FIG. 9 is a third schematic close-up view of an upper portion of a human face and the first array, in accordance with examples of the present disclosure.

FIG. 9 is a third schematic close-up view 900 of the first array 110 adjacent the nose 210 at the first angular artery (represented by a dashed line), in accordance with examples of the present disclosure. The first array 110 is illustrated as having three columns and five rows (3×5) of nodes 130*a*-130*o* (generically referred to as nodes 130).

The first array 110 is illustrated adjacent the nose 210 at the first angular artery 220, at a position corresponding to the location of the first nose pad region 160 (FIG. 1) of the wearable device 100 (FIG. 1) when worn in a first position.

The first angular artery 220 can be seen above the node 130*b* at the leftmost position of the first row of the first array 110, and above the nodes 130*a*, 130*cde*, at the respective middle positions of the second, third, fourth and fifth rows of the first array 110. It will be appreciated that the position of the first array 110 relative to the face 230 (and thus relative to the angular artery 220) is shifted when compared with the position of the first array 110 as shown in FIGS. 7 and 8.

The nodes 130*abcde* above the first angular artery 220 may be described as belonging to the first set, as the vasodilation sensed by the nodes 130*abcde* is higher than the vasodilation sensed by the remaining nodes of the first array 110. The remaining nodes may be described as one or more nodes not of the first set.

In the example shown by FIG. 9, the vasodilation sensed by the nodes above the first angular artery 220 (namely, the leftmost node of the first row and the respective middle nodes of the second, third, fourth and fifth rows) will be higher than the vasodilation sensed by the remaining nodes, due to the respective location of the first angular artery 220. The nodes sensing the higher vasodilation may be identified as a first set of one or more nodes of the first array 110. The remaining nodes may be described as one or more nodes not of the first set.

In this way, the first signal variation pattern may be defined as the relative level of vasodilation as illustrated by the highlighting of the nodes 130 in FIG. 9.

A comparison between the location of the first set of nodes of FIG. 9 and the first reference set of nodes of FIG. 8 indicates a downward and rightward (i.e., outward from the face) difference in location. As the first reference set of nodes corresponds to the location of first artery when the array is in the first reference position, and first set of nodes corresponds to the location of first artery when the array is in the first position, the downward and rightward difference in location may correspond to a movement of the nose bridge of the wearable device 100 (FIG. 1) down the nose 210 of the user.

In some examples, the first position of the first array relative to the first artery may be further determined by identifying a first node of the first set of one or more nodes of the first array.

In some examples, the first node may be described as a node having at least two neighbours belonging to the first set. In the example embodiment shown in FIG. 9, the node 130*a* at the middle position of the second row is highlighted to identify the node 130*a* as the first node. The first node is highlighted to indicate that the first node has at least two neighbours belonging to the first set. In other words, the middle node has been identified as having two or more neighbour nodes sensing a vasodilation higher than the vasodilation sensed by the nodes not of the first set. In the embodiment shown in FIG. 8, the node 130*b* at the leftmost position of the first row of the first array 110 and the node 130*c* at the middle position of the third row of the first array 110 are highlighted to indicate that these nodes 130*bc* represent two neighbours of the first node (the node 130*a* at the middle position of the second row) belonging to the first set. In this way, neighbourhoods of nodes and their spatial relationships over time may be used to track the relative position of an angular artery 220.

As noted, in some embodiments, the difference between the first position and the reference position may be determined based on a comparison between a location of the first node of the first set and a location of the first reference node of the first reference set.

A comparison between the location of the first node (i.e., the node 130*a* at the middle position of the second row) of FIG. 9 and the first reference node (i.e., the node 130*f* at the last position of the third row) of FIG. 8 indicates a downward and rightward difference in location. As the first reference node corresponds to the location of the first artery when the array is in the first reference position, and the first node corresponds to the location of the first artery when the array is in the first position, the downward and leftward difference in location may correspond to a movement of the nose bridge of the wearable device 100 (FIG. 1) down the nose 210 of the user. As the distances between each respective node (i.e., the distance between the node 130*a* and the node 130*f*) is known, the difference between the first position and the first reference position may be quantified.

Figure 10:
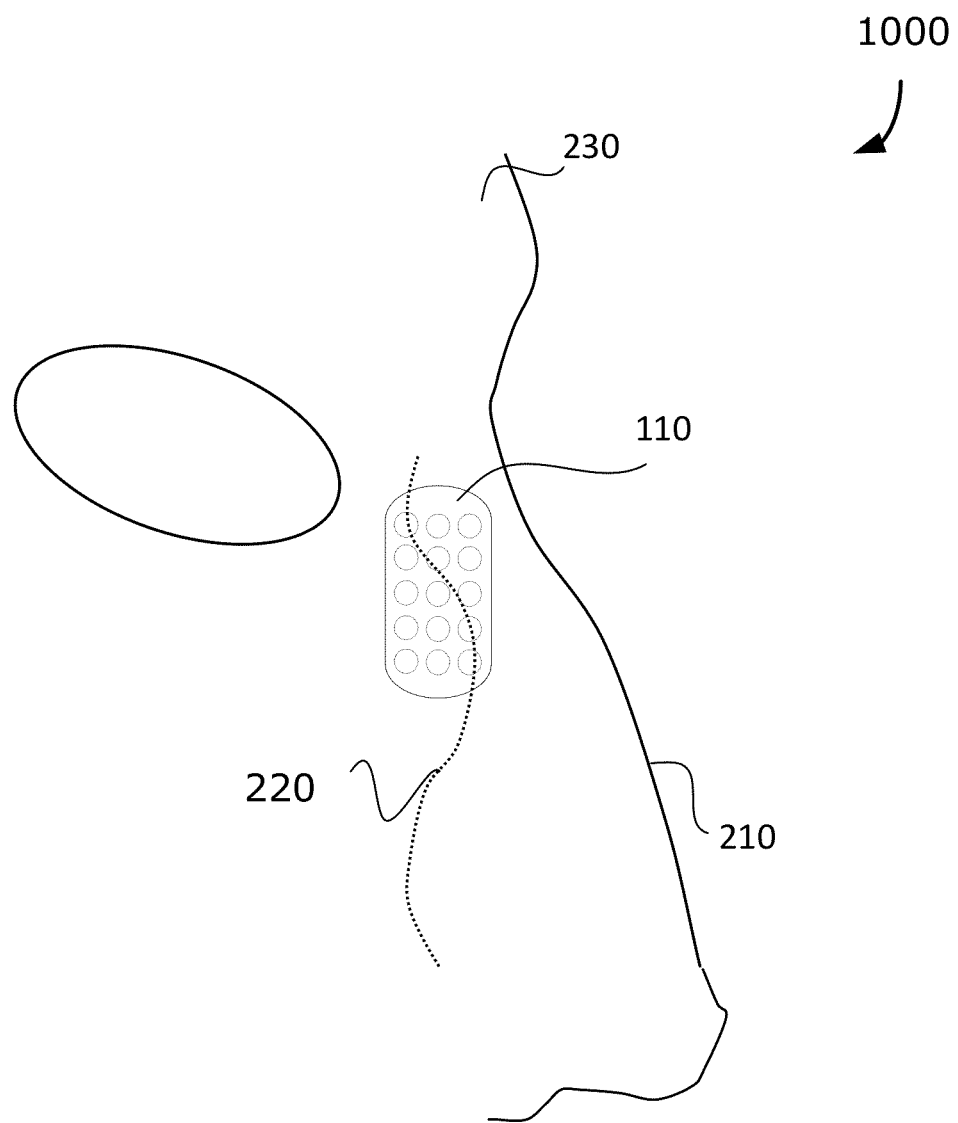
FIG. 10 is a first schematic profile view of an upper portion of a human face and the first array, in accordance with examples of the present disclosure.

Reference is now made to FIG. 10, which is a first schematic profile view 1000 of an upper portion of a human face 230 and the first array 110, in accordance with examples of the present disclosure. In the embodiment shown by FIG. 10, the first angular artery 220 is shown extending laterally along the nose 210, near the convergence of the nose 210 with the face 230.

The first array 110 is illustrated adjacent the nose 210 at the first angular artery 220, at a position corresponding to the location of the first nose pad region 160 (FIG. 1) of the wearable device 100 when the wearable device 100 is worn in a reference position on the face 230. In some embodiments, the reference position may correspond to a position of the wearable device 100 when worn on the face 230 for the first time. Additionally or alternatively, the reference position may be determined as part of a calibration process between the wearable device 100 and the face 230.

For example, an eye-tracking algorithm associated with the wearable device 100 may require a user to perform a calibration procedure when wearing the wearable device 100

(e.g., embodied as a pair of smart glasses) for the first time. In some examples, the calibration procedure may be used to implement an eye-tracking algorithm. In some examples, the calibration procedure may include requiring the user to look at a set of known point light sources (e.g. light emitting diodes (LEDs)) that are reflected in a captured image of the eye and are used to adapt the eye-tracking algorithm to the unique physiologically of the user's cornea.

The path of the first angular artery 220 with respect to the nodes of the first array 110 is shown in the schematic profile view 1000. The first angular artery 220 can be seen overlaid by the leftmost node of the first row of the first array 110, overlaid by the middle node of the second row of the first array 110, and overlaid by the respective last nodes of the third, fourth and fifth rows of the first array 110.

Figure 11:
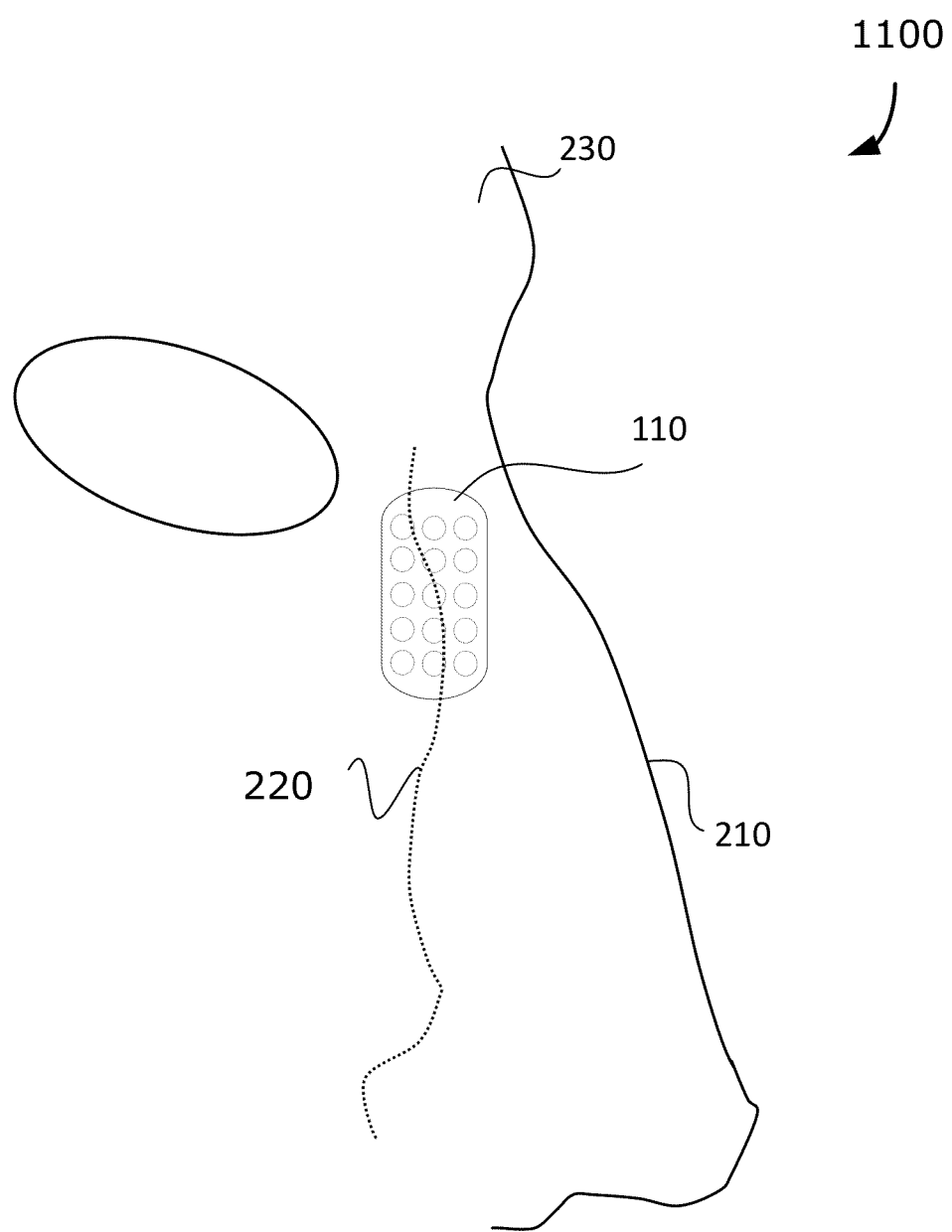
FIG. 11 is a second schematic profile view of the first array adjacent the nose at the first angular artery, in accordance with examples of the present disclosure.

Reference is now made to FIG. 11, which is a second schematic profile view 1100 of an upper portion of a human face 230 and the first array 110 in accordance with examples of the present disclosure. In the embodiment shown by FIG. 11, the first angular artery 220 is shown extending laterally along the nose 210, near the convergence of the nose 210 with the face 230.

The first array 110 is illustrated adjacent the nose 210 at the first angular artery 220, at a position corresponding to the location of the first nose pad region 160 (FIG. 1) of the wearable device 100 when the wearable device 100 is worn in a first position on the face 230. It will be appreciated that the position of the first array 110 relative to the face 230 (and thus relative to the angular artery 220) is shifted when compared with the position of the first array 110 as shown in FIG. 10.

Referring again to FIG. 1, in some embodiments, the wearable device 100 may include more than one array. For example, the wearable device 100 may include a first array 110 and a second array 120. As shown in FIG. 1, the first array 110 may be located at a first nose pad region 160 of the wearable device 100 and the second array 120 may be located at a second nose pad region 140 of the wearable device 100.

In some embodiments, operations comparable to those of the method 600 may be performed with respect to the second array 120.

Reference is now made to FIG. 12, which is a flowchart of an example method 1200 of determining a difference between a second position and a second reference position, in accordance with an embodiment of the present disclosure. The method 1200 may be performed by one or more processors of a computing system. Specifically, the operations 1210 and onward may be performed by one or more processors of a user device. The method 1200 may be performed by the computing system 400 of FIG. 4, for example by the processor 405 executing instructions stored in the memory 410, such as instructions of the wearable device location determination application 585.

In some embodiments, the method 600 of FIG. 6 and the method 1200 of FIG. 12 may be performed contemporaneously. In some embodiments, the method 600 of FIG. 6 and the method 1200 of FIG. 12 may be performed non-contemporaneously.

At the operation 1210, the computing system receives second reference signal information representing respective second reference signal variation data sensed by each node of a second array of non-optical sensing nodes. The second reference signal information may be received from a wearable device, and the second array of nodes may form part of the wearable device.

At the operation 1220, the computing system determines a second reference position of the second array relative to a second artery. The second reference position may be determined based on a second reference signal variation pattern in the second signal information. Various techniques for determining a reference signal variation pattern have been described previously and need not be repeated here.

In some embodiments, the second reference position of the second array relative to the second artery may be determined by identifying a second reference set of one or more nodes of the second array corresponding to the second artery.

At the operation 1230, the computing system receives second signal information representing respective second signal variation data sensed by each node of a second array of non-optical sensing nodes. The second signal information may be received from a wearable device, and the second array of nodes may form part of the wearable device.

At the operation 1240, the computing system determines a second position of the second array relative to a second artery. The second position may be determined based on a second signal variation pattern in the second signal information. Various techniques for determining a signal variation pattern have been described previously and need not be repeated here.

In some embodiments, the second position of the second array relative to the second artery may be determined by identifying a second set of one or more nodes of the second array corresponding to the location of the second artery.

At the operation 1250, the computing system determines a difference between the second position and the second reference position of the second array relative to the second artery.

In some embodiments, the difference between the second position and the second reference position may be determined based on a comparison between a location of the second set of one or more nodes in the second array and a location of the second reference set of one or more nodes in the first array, as described with reference to FIGS. 9 and 11 in the context of the method 600 of FIG. 6.

In some embodiments, the difference between the second position and the second reference position may be determined based on a comparison between a location of the second node of the second set and a location of the second reference node of the second reference set, as further described with reference to FIGS. 9 and 11 in the context of the method 600 of FIG. 6.

In some embodiments including both a first array and a second array, torque of the wearable device 100 may be determined based on the difference in the second signal information (compared to the second reference signal information) and the difference in the first signal information (compared to the first reference signal information. For example, if the second signal information exhibits a lower mean signal magnitude compared to the second reference signal information, and the first signal information exhibits a greater mean signal magnitude compared to the first reference signal information, this may indicate that the second array is being pressed against the side of the nose while the first array is further away, meaning that the wearable device 100 is likely to be torqued. Various techniques such as such as optical flow, keypoint matching, and siamese neural networks may be used to model a function that maps measurements from the first and second arrays to determine two-dimensional (2D) and/or three-dimensional (3D) positioning (e.g., determining a measurement of torque of the wearable device 100).

As noted, in some embodiments, the reference position may correspond to a position of the wearable device 100 when worn on the face 230 for the first time. Additionally or alternatively, the reference position may be determined as part of a calibration process between the wearable device 100 and the face 230.

In some embodiments, the second reference position may correspond to a position of the wearable device 100 when worn on the face 230 for the first time. Additionally or alternatively, the second reference position may be determined as part of a calibration process between the wearable device 100 and the face 230. In some embodiments, prior to performing the method 1200, the computing system may attempt to determine that the second array of the wearable device is positioned in proximity to a human artery.

In some embodiments, prior to performing the method 1200, the computing system may determine that the second reference signal information indicates a second low frequency signal similar to human heart activity. In some embodiments, the second reference position is determined in response to determining that the second reference signal information indicates the second low frequency signal similar to human heart activity.

In some embodiments, subsequent to determining that the first reference signal information indicates a first low frequency signal similar to human heart activity, and to determining that the second reference signal information indicates a second low frequency signal similar to human heart activity, the computing system may determine that the first low frequency signal and the second low frequency signal have similar magnitudes. In this way, the computing system may determine that the wearable device is located near first and second arteries of the user.

Referring again to FIG. 5, the application software 570 of the memory 410 of the computing system 400 (FIG. 3) adapts the example computing system 400, in combination with the operating system 580, to operate as a system performing a particular function. In some embodiments, as illustrated in FIG. 5, the application software 570 may comprise one or more of a wearable device location determination application 585 and/or an eye gaze signal tracking application 590. As noted, the example computing system 400 (FIG. 4) may be illustrative of both the user device 310 and the wearable device 100 shown in FIG. 3.

Figure 13:
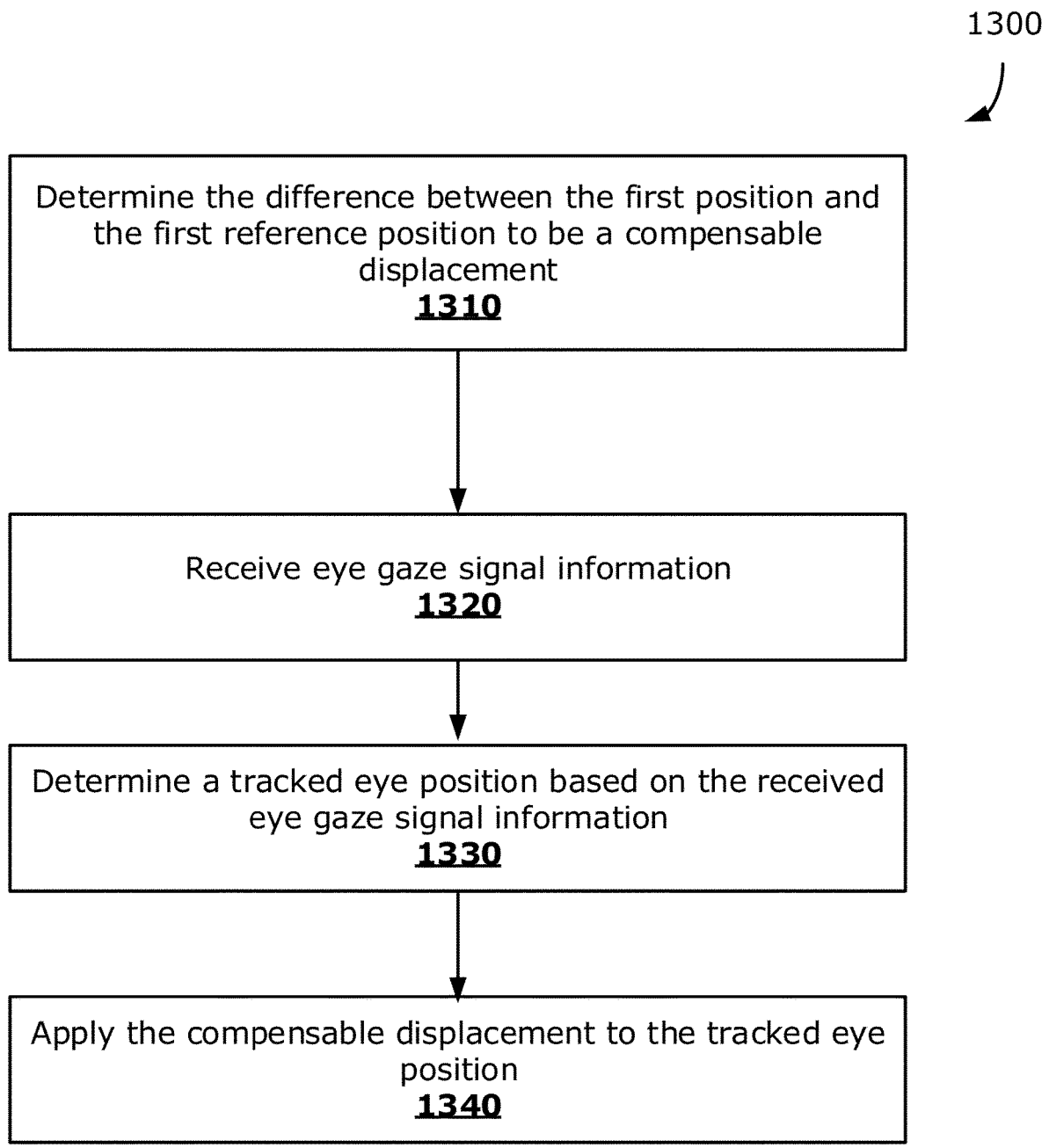
FIG. 13 is a flowchart of a method for applying a compensable difference to a tracked eye position, in accordance with examples of the present disclosure.

Reference is now made to FIG. 13, which is a flowchart of a method 1300 for applying a compensable difference to a tracked eye position, in accordance with examples of the present disclosure. The method 1300 may be performed by one or more processors of a computing system. Specifically, the operations 1310 and onward may be performed by one or more processors of a user device and/or one or more processors of a wearable device. The method 1300 may be performed by the computing system 400 of FIG. 4, for example by the processor 405 executing instructions stored in the memory 410, such as instructions of the wearable device location determination application 585.

At the operation 1310, the computing system determines the difference between the first position and the first reference position to be a compensable displacement. A compensable difference is a difference that may compensated for, without adjusting the physical position of the wearable device, by an eye gaze tracking application (e.g., by applying a compensation factor to a computed eye gaze vector).

At the operation 1320, the computing system receives eye gaze signal information. The eye gaze signal information may be received, for example, from an eye tracking device, which be or may include at least one camera 460 (FIG. 4) capable of capturing images of at least one eye of a user of the wearable device.

At the operation 1330, the computing system determines a tracked eye position based on the received eye gaze signal information. The tracked eye position may be based upon an assumption about the relative orientation between one or more eyes of the user and the wearable device. For example, the tracked eye position may be determined based upon an assumption that the wearable device is worn correctly.

At the operation 1340, the computing system applies the compensable displacement to the tracked eye position. In a particular simple example where the wearable device is a pair of smartglasses, the compensable difference may be determined to be equivalent to a 1 mm downward shift and a 2 mm outward shift. In this particular example, applying the compensable displacement to the tracked eye position would adjust the tracked eye position 1 mm upwards and 2 mm inwards.

A compensable displacement may also be applied in embodiments where both a first array and a second array are used.

In some embodiments, the difference between the first position and the first reference position may not be determined to be a compensable displacement. In some embodiments, the difference between the first position and the first reference position may be determined to be outside of a tolerance range. In some examples, where the difference is determined to be outside of a tolerance range, the difference may be too large to be effectively applied to the tracked eye position. In some such embodiments, following a determination that the difference between the first position and the first reference position is outside a tolerance range, the computing system may output a notification to adjust the wearable device. The notification may take a variety of forms, such as an audio notification and/or a visual notification displayed on the wearable device 100 and/or the user device 310.

A determination that the difference is outside of a tolerance range may also be made in embodiments where both a first array and a second array are used. A determination that the difference is outside of a tolerance range may also be made in examples involving advanced techniques such as optical flow, keypoint matching, and siamese neural networks to determine two-dimensional (2D) and/or three-dimensional (3D) positioning (e.g., determining a measurement of torque of the wearable device). In examples where both a first array and a second array are used, the computing system may output a notification to adjust the wearable device. The notification may take a variety of forms, such as an audio notification and/or a visual notification displayed on the wearable device 100 and/or the user device.

Although the present disclosure describes methods and processes with steps in a certain order, one or more steps of the methods and processes may be omitted or altered as appropriate. One or more steps may take place in an order other than that in which they are described, as appropriate.

Although the present disclosure is described, at least in part, in terms of methods, a person of ordinary skill in the art will understand that the present disclosure is also directed to the various components for performing at least some of the aspects and features of the described methods, be it by way of hardware components, software or any combination of the two. Accordingly, the technical solution of the present disclosure may be embodied in the form of a software product. A suitable software product may be stored in a pre-recorded storage device or other similar non-volatile or non-transitory computer readable medium, including DVDs, CD-ROMs, USB flash disk, a removable hard disk, or other storage media, for example. The software product includes instructions tangibly stored thereon that enable a processing device (e.g., a personal computer, a server, or a network device) to execute examples of the methods disclosed herein.

The present disclosure may be embodied in other specific forms without departing from the subject matter of the claims. The described example embodiments are to be considered in all respects as being only illustrative and not restrictive. Selected features from one or more of the above-described embodiments may be combined to create alternative embodiments not explicitly described, features suitable for such combinations being understood within the scope of this disclosure.

All values and sub-ranges within disclosed ranges are also disclosed. Also, although the systems, devices and processes disclosed and shown herein may comprise a specific number of elements/components, the systems, devices and assemblies could be modified to include additional or fewer of such elements/components. For example, although any of the elements/components disclosed may be referenced as being singular, the embodiments disclosed herein could be modified to include a plurality of such elements/components. The subject matter described herein intends to cover and embrace all suitable changes in technology.

The invention claimed is:

1. A wearable device comprising:
   a first array of non-optical sensing nodes, the first array comprising a plurality of nodes, the first array being positioned at a first side of a nose bridge of the wearable device,
   wherein the plurality of nodes are operable to sense vasodilation of an artery in proximity to the first array.

2. The wearable device of claim 1, wherein the non-optical sensing nodes comprise at least one of capacitive sensing nodes or vibration sensing nodes.

3. The wearable device of claim 1, wherein the wearable device further comprises a second array of non-optical sensing nodes, the second array comprising another plurality of nodes, and wherein the second array is positioned at a second side of the nose bridge of the wearable device.

4. The wearable device of claim 1, wherein the wearable device is a pair of smartglasses, or an extended reality (XR) headset.

5. The wearable device of claim 1, further comprising a wireless communication interface configured to transmit signal information representing data sensed by the first array to a computing system.

6. The wearable device of claim 1, wherein the plurality of nodes in the first array are arranged in at least two columns and at least two rows.

7. A computer-implemented method comprising:
   receiving first signal information representing respective first signal variation data sensed by each node of a first array of non-optical sensing nodes of a wearable device;
   determining a first position of the first array relative to a first artery based on a first signal variation pattern in the first signal information; and
   determining a difference between the first position and a first reference position of the first array relative to the first artery.

8. The method of claim 7, wherein the difference between the first position and the first reference position is determined to be a compensable displacement, and wherein the method further comprises:
   applying the compensable displacement to a tracked eye position.

9. The method of claim 8, wherein prior to applying the compensable displacement to the tracked eye position, the method further comprises:
   receiving eye gaze signal information; and
   determining the tracked eye position based on the received eye gaze signal information.

10. The method of claim 7, wherein the difference between the first position and the first reference position is determined to be outside of a tolerance range; and wherein the method further comprises:
    outputting a notification to adjust the wearable device.

11. The method of claim 7, wherein the method further comprises, prior to receiving the first signal information:
    receiving first reference signal information representing respective first reference signal variation data sensed by each node of the first array of non-optical sensing nodes of the wearable device; and
    determining a first reference position of the first array relative to a first artery based on a first reference signal variation pattern in the first reference signal information.

12. The method of claim 11, wherein the method further comprises, prior to determining the first reference position:
    determining that the first reference signal information indicates a first low frequency signal similar to human heart activity,
    wherein the first reference position is determined in response to determining that the first reference signal information indicates the first low frequency signal similar to human heart activity.

13. The method of claim 11, wherein the method further comprises:
    receiving second signal information representing respective second signal variation data sensed by each node of a second array of non-optical sensing nodes of the wearable device;
    determining a second position of the second array relative to a second artery based on a second signal variation pattern in the second signal information; and
    determining a difference between the second position and a second reference position of the second array relative to the second artery.

14. The method of claim 13, wherein the method further comprises, prior to determining the second signal information from the second array of non-optical sensing nodes:
    receiving second reference signal information representing respective second reference signal variation data sensed by the second array of non-optical sensing nodes of the wearable device; and
    determining the second reference position of the second array relative to the second artery based on a second reference signal variation pattern in the second reference signal information.

15. The method of claim 14, wherein prior to determining the second reference position, the method further comprises:
    determining that the first reference signal information indicates a first low frequency signal similar to human heart activity;
    determining that the second reference signal information indicates a second low frequency signal similar to human heart activity; and determining that the first low frequency signal and the second low frequency signal have similar magnitudes.

16. The method of claim 11,
wherein the first position of the first array relative to the first artery is determined by:
generating a first matrix of measurements based on the first signal information;
wherein the first reference position of the first array relative to the first artery is determined by:
generating a first reference matrix of measurements based on the first reference signal information; and
wherein the difference between the first position and the first reference position is determined based on a comparison between the first matrix and the first reference matrix.

17. The method of claim 11,
wherein the first position is determined by:
identifying a first set of one or more nodes of the first array, wherein the respective first signal variation data sensed by each node of the first set indicates higher signal variation than the respective first signal variation data sensed by each of the one or more nodes not of the first set; and
wherein the first reference position is determined by:
identifying a first reference set of one or more nodes of the first array, wherein the respective first reference signal variation data sensed by the one or more nodes of the first reference set indicates higher signal variation than the respective first reference signal variation data sensed one or more nodes not of the first reference set.

18. The method of claim 17,
wherein the difference between the first position and the first reference position is determined based on a comparison between a location of the first set of one or more nodes in the first array and a location of the first reference set of one or more nodes in the first array.

19. The method of claim 17,
wherein the first position is further determined by:
identifying a first node of the first set, the first node having two or more neighbour nodes belonging to the first set;
wherein the first reference position is determined by:
identifying a first reference node of the first reference set, the first reference node having two or more neighbour nodes belonging to the first reference set; and
wherein the difference between the first position and the first reference position is determined based on a comparison between a location of the first node of the first set and a location of the first reference node of the first reference set.

20. The method of claim 7, wherein the method is performed by the wearable device.

21. A device comprising:
a processor; and
a memory coupled to the processor, the memory storing instructions which, when executed by the processor, cause the device to:
receive first signal information representing respective first signal variation data sensed by each node of a first array of non-optical sensing nodes of a wearable device;
determine a first position of the first array relative to a first artery based on a first signal variation pattern in the first signal information; and
determine a difference between the first position and a first reference position of the first array relative to the first artery.

22. The device of claim 21, wherein the device is a wearable device.

* * * * *